US011534526B2

(12) United States Patent
Luukko et al.

(10) Patent No.: US 11,534,526 B2
(45) Date of Patent: Dec. 27, 2022

(54) MEDICAL HYDROGEL

(71) Applicant: UPM-Kymmene Corporation, Helsinki (FI)

(72) Inventors: Kari Luukko, Espoo (FI); Markus Nuopponen, Helsinki (FI)

(73) Assignee: UPM-KYMMENE CORPORATION, Helsinki (FI)

(*) Notice: Subject to any disclaimer, the term of this patent is extended or adjusted under 35 U.S.C. 154(b) by 810 days.

(21) Appl. No.: 16/465,211

(22) PCT Filed: Dec. 14, 2017

(86) PCT No.: PCT/FI2017/050888
§ 371 (c)(1),
(2) Date: May 30, 2019

(87) PCT Pub. No.: WO2018/109275
PCT Pub. Date: Jun. 21, 2018

(65) Prior Publication Data
US 2019/0336643 A1    Nov. 7, 2019

(30) Foreign Application Priority Data
Dec. 15, 2016    (EP) .................................... 16397536

(51) Int. Cl.
A61L 26/00 (2006.01)
C08J 3/075 (2006.01)
C08L 1/02 (2006.01)

(52) U.S. Cl.
CPC ......... *A61L 26/008* (2013.01); *A61L 26/0023* (2013.01); *A61L 26/0066* (2013.01); *C08J 3/075* (2013.01); *C08L 1/02* (2013.01); *A61L 2400/12* (2013.01)

(58) Field of Classification Search
None
See application file for complete search history.

(56) References Cited

U.S. PATENT DOCUMENTS

2013/0330379 A1* 12/2013 Ylipertula ................ C08J 3/075
                                                          514/781
2016/0176989 A1    6/2016 Laukkanen et al.

FOREIGN PATENT DOCUMENTS

| JP | H11322803 A | 11/1999 |
| WO | 2014128354 | 2/2014 |
| WO | 2016102764 A1 | 6/2016 |
| WO | 2016102769 | 6/2016 |
| WO | 2016177395 | 11/2016 |
| WO | 2016177398 A1 | 11/2016 |

OTHER PUBLICATIONS

Lauren, P., Lou, Y. R., Raki, M., Urtti, A., Bergström, K., & Yliperttula, M. (2014). Technetium-99m-labeled nanofibrillar cellulose hydrogel for in vivo drug release. European Journal of Pharmaceutical Sciences, 65, 79-88. (Year: 2014).*
International Search Report for International Application No. PCT/FI2017/050888; International filing date Dec. 14, 2017; dated Jun. 21, 2018; 5 pages.
Written Opinion of the International Searching Authority for International Application No. PCT/FI2017/050888; International filing date: Dec. 14, 2017; dated Jun. 21, 2018; 10 pages.
Rudraraju, V. S. et al., "Rheological characterization of Microcrystalline Cellulose/Sodiumcarboxymethyl cellulose hydrogels using a controlled stress rheometer: part I," International Journal of Pharmaceutics, vol. 292, Issues: 1-2, Mar. 2005; pp. 53-61.

* cited by examiner

*Primary Examiner* — Dale R Miller
(74) *Attorney, Agent, or Firm* — Cantor Colburn LLP

(57) ABSTRACT

The present application relates to a medical hydrogel comprising nanofibrillar cellulose, wherein the hydrogel has a viscosity in the range of 2500-9000 Pa·s and a water retention value in the range of 30-100 g/g. The present application also relates to a method for preparing the medical hydrogel The present application relates to the medical hydrogel for use for treating wounds.

16 Claims, 4 Drawing Sheets

MEDICAL HYDROGEL

CROSS-REFERENCE TO RELATED APPLICATIONS

This application is a National Stage application of PCT/FI2017/050888, filed De. 14, 2017, which claims the benefit of European Application No. 16397536.0, filed Dec. 15, 2016, both of which are incorporated by reference herein in their entirety.

FIELD OF THE APPLICATION

The present application relates to a medical hydrogel comprising nanofibrillar cellulose and to said medical hydrogel for use for treating wounds.

BACKGROUND

Gels, such as hydrogels, may be used in medical applications, such as for covering skin and tissue. In general medical hydrogels are crosslinked materials containing mainly synthetic polymers. Synthetic hydrogels may be synthesized from hydrophilic monomers by either chain or step growth, along with a functional crosslinker to promote network formation. Such materials may be stretchy, flexible and sticky and may be attached to a target very tightly.

Also biological hydrogels are known which are derived from preexisting components of body tissues such as collagen, hyaluronic acid (HA), or fibrin. In order to mechanically enhance collagen into a hydrogel, it must be chemically crosslinked, crosslinked using UV light or temperature, or mixed with other polymers.

There are certain drawbacks in the existing medical hydrogels, such as the problems in handling the gels. Stickiness of the gels complicates the application of the gel by hands, and it may be difficult to remove the gels as intact for example from wound. Some gels may cover the target too effectively which may hinder the healing of a damaged area. Synthetic gels may not be compatible with biological tissues.

SUMMARY

In the present embodiments it was found that a hydrogel made of nanofibrillar cellulose could be applied to a variety of medical targets and it exhibited properties which are ideal for medical purposes.

One embodiment provides a medical hydrogel comprising nanofibrillar cellulose, wherein the hydrogel as provided has a viscosity in the range of 2500-9000 Pa·s at and a water retention value in the range of 30-100 g/g.

One embodiment provides a method for preparing a medical hydrogel, the method comprising
  providing pulp,
  disintegrating the pulp until nanofibrillar cellulose is obtained,
  forming the nanofibrillar cellulose into a hydrogel, wherein the hydrogel has a viscosity in the range of 2500-9000 Pa·s, such as 3000-8000 Pa·s, for example 4000-7000 Pa·s, and a water retention value in the range of 30-100 g/g, such as 30-60 g/g, preferably 40-50 g/g.

One embodiment provides a medical hydrogel for use for treating wounds.

One embodiment provides a kit containing the medical hydrogel packed in one or more sealed packages.

It was found out that a hydrogel comprising nanofibrillar cellulose and having certain physical properties at specific ranges was especially suitable for medical purposes, especially as a medical product, such as a dressing, a patch or a filter. When applied to a skin, especially to a wound, the hydrogel exhibited properties such as solidity, low stickiness, sufficient fracture toughness expressed as compression work, formability, and good removability or detachability. Further, the material may promote healing of a wound or other injury.

Certain advantageous properties of the hydrogel comprising nanofibrillar cellulose include flexibility, elasticity and remouldability. As the hydrogel contains a lot of water, it may also show good diffusion and release properties of molecules. These properties are useful for example when the hydrogel is used as a cover for healing wounds, or in other medical applications, such as for delivering therapeutic or cosmetic agents.

Solidity refers to a property which gives the hydrogel an ability to resist breaking or chipping. The solidity may be evaluated for example by the compression work of the gel, which may be also called as toughness.

Toughness is a feature which also affects to other properties of the hydrogel, such as the removability. The compression work correlates to the toughness of the gel. With high compression work the hydrogel is not prone to chip or break when handled, for example detached from a wound or a skin as intact as possible. Another feature affecting to the removability or the detachability is the high water retention value. A hydrogel containing a high amount of water is stable and mouldable.

The stickiness of the hydrogel is low, especially with gels with high concentration over 4% (w/w) or more. Low stickiness is desired, so that the gel will not stick to the user's skin when applying the gel to a target. One feature which may correlate with low stickiness is water retention value. In general, the higher the water retention value, the less sticky the gel is. High water retention is desired because in such case the cohesion between the water molecules and the nanofibers in high.

Also the viscosity of the hydrogel, as provided i.e. at its own concentration, was found to have an effect to the mouldability, removability and stickiness of the product. If the viscosity is too low the hydrogel tends to be sticky. On the other hand, if the viscosity is too high the gel tends to chip or break.

Flexibility is a feature which is desired in many applications, such as in medical applications. For example flexible patches and dressings comprising nanofibrillar cellulose hydrogel are useful for applying onto skin, for example for covering wounds and other damages or injuries, such as burns. A related desired feature is mouldability, especially when the hydrogel is to be applied to a deep wound. Viscosity in general correlates with the mouldability. The viscosity must be high enough so that the structure of the composition is maintained, but on the other hand low enough to enable mouldability and to prevent cracking of the gel. Further, with an optimal initial viscosity the viscosity of the pseudoplastic product decreases during moulding to facilitate the moulding of the gel into a desired form.

To characterize the desired properties of a hydrogel a combination of the features described herein may be used. Especially it was found out that the viscosity of the hydrogel and the water retention properties, such as water retention value, at the ranges claimed and described herein have great effects to the properties of the hydrogel. Such a nanofibrillar cellulose hydrogel is ideal as a medical hydrogel. The water retention must be in a such range that the product does not feel wet but on the other hand it forms a water layer between the product and the skin of wound to which is applied to, which water layer promotes the healing.

The hydrogels of the embodiments also provide high water retention capacity and molecule diffusion property speed, which properties are desired in medical applications such as wound treatment and the like. Large hydrogels may be prepared and/or shaped which may be used for covering large areas.

The hydrogels described herein are useful in medical applications, wherein the materials comprising nanofibrillar cellulose are in contact with living tissue. It was discovered that nanofibrillar cellulose provides unusual properties when it is applied for example onto skin or onto a damaged area. The products containing nanofibrillar cellulose as described herein are highly biocompatible with the living tissue and provide several advantageous effects. Without binding to any specific theory, it is believed that a hydrogel comprising very hydrophilic nanofibrillar cellulose having a very high specific surface area, and thus high water retention ability, when applied against a skin or other tissue, provides favourable moist environment between the tissue or wound and the nanofibrillar cellulose. The high amount of free hydroxyl groups in the nanofibrillar cellulose forms hydrogen bonds between the nanofibrillar cellulose and water molecules and enables gel formation and the high water retention ability of the nanofibrillar cellulose. Because of the high amount of water in the nanofibrillar cellulose hydrogel, only water is supposed to be in contact with tissue, and which also enables migration of fluids and/or agents from the wound to the hydrogel, or from the hydrogel to the wound.

When the hydrogels are used for covering wounds or other damages or injuries, several effects are provided. The usability of the products is good as the product may be applied and removed easily without being damaged, for example torn. The hydrogel protects the wound from infection and keeps moist environment for the wound to heal. The hydrogel will not attach to a damaged skin or wound in such irreversible way as conventional materials, which are usually very difficult to remove without damaging the healed area. The conditions between the product and the skin facilitate the healing of a damaged area.

The medical hydrogels of the embodiments are especially advantageous in the treatment of wounds, such as deep wounds. The may also be used for treating grafts, such as a skin graft. The hydrogel may be used for covering a wound or a graft area and it acts as a protective layer.

The hydrogels may also be used for controllably and effectively delivering agents, such as therapeutic or cosmetic agents, to a subject, such as a patient or a user, for example by transdermal route or by other route. The controlled release refers for example to obtaining a desired release rate and/or profile of an agent or agents over a time period, which may be affected by the selection of the gel, for example the percentage of the gel or the thickness of the gel, the concentration or form of the releasable agent(s), presence of any auxiliary agents, or other conditions, such as pH, temperature and the like having an effect to the release rate and/or activity of the releasable agents. The combined effect of the special conditions between the tissue and the hydrogel as explained in previous and the release properties provides efficient delivery of substances into living tissue. The nanofibrillar cellulose hydrogel provides a hydrophilic matrix, which is non-toxic, biocompatible and also biodegradable. For example the matrix may be degraded enzymatically. On the other hand the hydrogel is stable at physiological conditions.

BRIEF DESCRIPTION OF THE DRAWINGS

The embodiments will be explained in the following with reference to the appended drawings, where.

DETAILED DESCRIPTION

Figure 1:
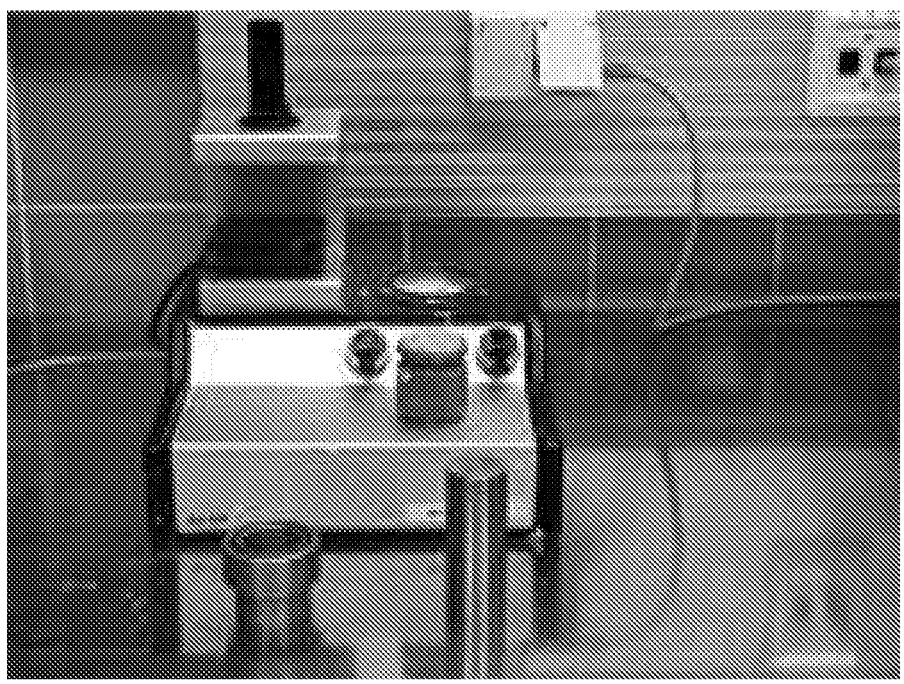
FIG. 1 shows an ÅAGWR device used in the tests

The present disclosure provides hydrogels comprising nanofibrillar cellulose, which may be also called as nanofibrillar cellulose hydrogels. The hydrogels may be provided as products, which may contain also other substances or other elements, such as reinforcing materials, covering materials, active agents, salts or the like. The hydrogels may be also provided or called as medical hydrogels or medical products. In one embodiment the hydrogel is provided as such, preferably containing only or substantially only nanofibrillar cellulose and water, such as a product containing 99% (w/w) of nanofibrillar cellulose and water, or more, such as 99.5% (w/w) or 99.9% (w/w), up to 100%.

The term "medical" refers to a product or use wherein the product, i.e. a product comprising the hydrogel of the embodiments, is used or is suitable for medical purposes. A medical product may be sterilized, or it is sterilisable, for example by using temperature, pressure, moisture, chemicals, radiation or a combination thereof, i.e. the product tolerates the sterilization treatment. The product may be for example autoclaved, or other methods using high temperature may be used, in which cases the product should tolerate high temperatures over 100° C., for example at least 121° C. or 134° C. In one example the product is autoclaved at 121° C. for 15 minutes. It is also desired that a medical product is pyrogen free and it does not contain undesired protein residues or the like. Also UV sterilization may be used. A medical product may also be suitable for example for cosmetic purposes, so it may be used also as a cosmetic product.

The nanofibrillar cellulose (NFC) hydrogel of the embodiments, such as anionic NFC hydrogel, is also able to controllably release active agents, such as therapeutic agents, for example pharmaceutical ingredients, as a function of time, especially when the temperature and pH are constant.

In this specification, percentage values, unless specifically indicated otherwise, are based on weight (w/w). If any numerical ranges are provided, the ranges include also the upper and lower values.

The starting material for preparing the hydrogels comprises nanofibrillar cellulose, which comprises or consists of cellulose fibrils having diameter at a submicron range, more particularly at a nanoscale range. It forms a self-assembled hydrogel network even at low concentrations. These gels of nanofibrillar cellulose are highly shear thinning and pseudoplastic in nature, which makes them different from conventional non-fibrillar cellulosic gels.

Nanofibrillar Cellulose

The nanofibrillar cellulose is prepared normally from cellulose raw material of plant origin. The raw material may be based on any plant material that contains cellulose. The raw material may also be derived from certain bacterial fermentation processes. The nanofibrillar cellulose is preferably made of plant material. In one example the fibrils are obtained from non-parenchymal plant material. In such case the fibrils may be obtained from secondary cell walls. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. One abundant source of such cellulose fibrils is wood fibres. In one embodiment the plant material is wood. Wood was found to be especially suitable for the medical applications. Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one embodiment the nanofibrillar cellulose is obtained from wood pulp. In one embodiment the nanofibrillar cellulose is obtained from hardwood pulp. In one example the hardwood is birch. In one embodiment the nanofibrillar cellulose is obtained from softwood pulp.

The nanofibrillar cellulose is manufactured by homogenizing wood-derived fibrous raw material, which may be chemical pulp. Cellulose fibers are disintegrated to produce fibrils which have the diameter of only some nanometers, which is 50 nm at the most and gives a dispersion of fibrils in water. The fibrils may be reduced to size where the diameter of most of the fibrils is in the range of 2-50 nm, more particularly in the range of only 2-20 nm.

As used herein, the term "nanofibrillar cellulose" refers to cellulose fibrils or fibril bundles separated from cellulose-based fiber raw material. These fibrils are characterized by a high aspect ratio (length/diameter): their length may exceed 1 μm, whereas the diameter typically remains smaller than 200 nm. The smallest fibrils are in the scale of so-called elementary fibrils, the diameter being typically in the range of 2-12 nm. The dimensions and size distribution of the fibrils depend on the refining method and efficiency. Nanofibrillar cellulose may be characterized as a cellulose-based material, in which the median length of particles (fibrils or fibril bundles) is not greater than 50 μm, for example in the range of 1-50 μm, and the particle diameter is smaller than 1 μm, suitably in the range of 2-500 nm. In case of native nanofibrillar cellulose, in one embodiment the average diameter of a fibril is in the range of 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose may also contain small amounts of other wood components, such as hemicellulose or lignin. The amount is dependent on the plant source. Often used parallel names for nanofibrillar cellulose include nanofibrillated cellulose (NFC) and nanocellulose.

Different grades of nanofibrillar cellulose may be categorized based on three main properties: (i) size distribution, length and diameter (ii) chemical composition, and (iii) rheological properties. To fully describe a grade, the properties may be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low, low viscosity vs. high viscosity etc. The fibrillation technique and the chemical pre-modification have an influence on the fibril size distribution. Typically, non-ionic grades have wider fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood (HW) vs. softwood (SW) pulp, different polysaccharide composition exists in the final nanofibrillar cellulose product. Commonly, the non-ionic grades are prepared from bleached birch pulp, which yields high xylene content (25% by weight). Modified grades are prepared either from HW or SW pulps. In those modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

In an aqueous environment, a dispersion of cellulose nanofibers forms a viscoelastic hydrogel network. The gel is formed already at relatively low concentrations of, for example, 0.05-0.2% (w/w) by dispersed and hydrated entangled fibrils. The viscoelasticity of the NFC hydrogel may be characterized, for example, with dynamic oscillatory rheological measurements.

The nanofibrillar cellulose hydrogels exhibit characteristic rheological properties. For example they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

In one example the disintegration is carried out by using a disperser having at least one rotor, blade or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives several successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is usually a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be, for example, Brookfield viscosity or zero shear viscosity.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used.

The nanofibrillar cellulose provided as a starting material may be characterized by the viscosity it provides in a water solution. The viscosity describes, for example, the fibrillation degree of the nanofibrillar cellulose.

In one embodiment the nanofibrillar cellulose when dispersed in water provides a Brookfield viscosity of at least 500 mPa·s, such as at least 1000 mPa·s, at least 1500 mPa·s, at least 2000 mPa·s, or at least 3000 mPa·s, measured at a consistency of 0.8% (w/w) and at 10 rpm. In one embodiment the nanofibrillar cellulose, when dispersed in water, provides a Brookfield viscosity of at least 5000 mPa·s measured at a consistency of 0.8% (w/w) and at 10 rpm. Examples of Brookfield viscosity ranges of said nanofibrillar cellulose when dispersed in water include 500-10000 mPa·s, 500-8000 mPa·s, 1000-10000 mPa·s, 2000-10000 mPa·s, 1000-8000 mPa·s, 500-15000 mPa·s, 1000-15000 mPa·s, 2000-15000 mPa·s, 1000-20000 mPa·s, measured at a consistency of 0.8% (w/w) and at 10 rpm.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, that is, pulp.

The modification treatment to the fibers may be chemical or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface. The modification treatment may also be enzymatic.

The cellulose in the fibers may be especially ionically charged after the modification, because the ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. A cationic charge in turn may be created chemically by cationization by attaching a cationic group to the cellulose, such as quaternary ammonium group.

In one embodiment the nanofibrillar cellulose comprises chemically modified nanofibrillar cellulose, such as anionically modified nanofibrillar cellulose or cationically modified nanofibrillar cellulose. In one embodiment the nanofibrillar cellulose is anionically modified nanofibrillar cellulose. In one embodiment the nanofibrillar cellulose is cationically modified nanofibrillar cellulose. In one embodiment the anionically modified nanofibrillar cellulose is oxidized nanofibrillar cellulose. In one embodiment the anionically modified nanofibrillar cellulose is sulphonized nanofibrillar cellulose. In one embodiment the anionically modified nanofibrillar cellulose is carboxymethylated nanofibrillar cellulose.

The cellulose may be oxidized. In the oxidation of cellulose, the primary hydroxyl groups of cellulose may be oxidized catalytically by a heterocyclic nitroxyl compound, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The nanofibrillar cellulose may also be characterized by the average diameter (or width), or by the average diameter together with the viscosity, such as Brookfield viscosity or zero shear viscosity. In one embodiment said nanofibrillar cellulose has a number average diameter of a fibril in the range of 1-100 nm. In one embodiment said nanofibrillar cellulose has a number average diameter of a fibril in the range of 1-50 nm. In one embodiment said nanofibrillar cellulose has a number average diameter of a fibril in the range of 2-15 nm, such as TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose these ranges may be combined with the viscosity ranges of the nanofibrillar cellulose, for example wherein the nanofibrillar cellulose, when dispersed in water, provides a Brookfield viscosity of at least 2000 mPa·s, such as at least 10000 mPa·s, for example at least 15000 mPa·s measured at a consistency of 0.8% (w/w) and at 10 rpm.

Medical Hydrogel

One embodiment provides a medical hydrogel comprising nanofibrillar cellulose, wherein the hydrogel has a viscosity in the range of 2500-9000 Pa·s and a water retention value in the range of 30-100 g/g.

One embodiment provides a method for preparing a medical hydrogel, the method comprising
providing pulp,
optionally modifying the pulp,
disintegrating the pulp until nanofibrillar cellulose is obtained,
forming the nanofibrillar cellulose into a hydrogel, wherein the hydrogel has a viscosity in the range of 2500-9000 Pa·s, such as 3000-8000 Pa·s, for example 4000-7000 Pa·s, and a water retention value in the range of 30-100 g/g, such as 30-60 g/g, preferably 40-50 g/g.

The pulp may be any suitable pulp disclosed herein. In one embodiment the pulp is wood pulp. The pulp may be modified, for example chemically of enzymatically. The chemically modified pulp may be cationically or anionically modified. In one embodiment the pulp is anionically modified wood pulp.

The pulp is disintegrated into nanofibrillar cellulose, usually as an aqueous dispersion, which may be separately characterized for example by using rheological properties, such as viscosity, as described herein. Any additional substances, such as therapeutic agents, cosmetic agents or other agents or substances may be added to the obtained nanofibrillar cellulose to obtain a mixture of nanofibrillar cellulose and one or more of the agent(s) or substance(s). The fibrillation is carried out to a such extent that the desired properties, such as the viscosity at the own concentration and the compression work, are obtained. Such a fibrillation procedure may include a certain number of disintegration or fibrillations runs, certain fibrillation time or speed, or the like process parameters.

One embodiment provides a method for preparing a medical hydrogel, the method comprising
providing nanofibrillar cellulose,
forming the nanofibrillar cellulose into a hydrogel, wherein the hydrogel has a viscosity in the range of 2500-9000 Pa·s, such as 3000-8000 Pa·s, for example 4000-7000 Pa·s, and a water retention value in the range of 30-100 g/g, such as 30-60 g/g, preferably 40-50 g/g.

The nanofibrillar cellulose is formed into a hydrogel having the desired properties. The "forming" may include for example concentrating, fibrillating, homogenizing, adding any further agents or substances, or any other actions to obtain the desired properties.

In one embodiment the method comprises homogenizing the obtained or provided nanofibrillar cellulose in a non-fibrillating homogenization. This treatment removes the discontinuities in the fibrillated nanofibrillar cellulose but does not further fibrillate the material. The homogenization enhances the properties of the final product so the usability of the medical hydrogel is optimal for the intended use.

In one embodiment the hydrogel has a viscosity in the range of 3000-8000 Pa·s. In one embodiment the hydrogel has a viscosity in the range of 4000-7000 Pa·s, These viscosities are measured at the concentration of the hydrogel as provided, i.e. "at own concentration", which may be in the range of 4-8% (w/w), as described herein. The viscosities at own concentration may be measured with any suitable viscometer, and are different from Brookfield viscosity. In the tests the viscosities were measured with HAAKE Viscotester iQ Rheometer (Thermo Fisher Scientific, Karlsruhe, Germany) equipped with a Peltier system for temperature control.

Preferably the hydrogel has a solids content, which is also called as dry matter content, over 4% (w/w), such as at least 4.1% (w/w). In one embodiment the hydrogel has a solids content in the range of 4.1-8% (w/w). In one embodiment the hydrogel has a solids content in the range of 4.5-8% (w/w). In one embodiment the hydrogel has a solids content in the range of 5-8% (w/w). In one embodiment the hydrogel has a solids content in the range of 5-7% (w/w). In one embodiment the hydrogel has a solids content in the range of 6-8% (w/w). In one embodiment the hydrogel has a solids content in the range of or 6-7% (w/w). Such solids content is relatively high for a nanofibrillar material, which in general forms a gel at very low concentrations. However, the high solids content was found to provide advantageous properties for the medical uses.

In one embodiment the hydrogel has a water retention value in the range of 30-60 g/g. In one embodiment the hydrogel has a water retention value in the range of 40-50 g/g. The "g/g" refers to grams of water to a gram of hydrogel. Therefore the nanofibrillar hydrogel may contain up to 100 grams of water per one gram of dry hydrogel, which is generally not possible for conventional gel forming materials. The tested gels had water retention value in the range of 40-50 g/g which was found to provide advantageous properties for the intended purposes. Especially the high water content of the gel provided such toughness for the gel that it could be handled and for example detached from a wound without breaking the gel. The water retention was measured with ÅAGWR water retention method (Åbo Akademi Gravitometric Water Retention), which is a coating colour static water retention method useful for nanofibrillar cellulose. In general conventional water retention measuring methods cannot be used for nanofibrillar cellulose having such high water content.

In one embodiment the hydrogel has a viscosity in the range of 3000-8000 Pa·s, and a water retention value in the range of 30-100 g/g. In one embodiment the hydrogel has a viscosity in the range of 4000-7000 Pa·s and a water retention value in the range of 30-100 g/g. In one embodiment the hydrogel has a viscosity in the range of 2500-9000 Pa·s and a water retention value in the range of 30-60 g/g. In one embodiment the hydrogel has a viscosity in the range of 3000-8000 Pa·s, and a water retention value in the range of 30-60 g/g. In one embodiment the hydrogel has a viscosity in the range of 4000-7000 Pa·s and a water retention value in the range of 30-60 g/g. In one embodiment the hydrogel has a viscosity in the range of 2500-9000 Pa·s and a water retention value in the range of 40-50 g/g. In one embodiment the hydrogel has a viscosity in the range of 3000-8000 Pa·s, and a water retention value in the range of 40-50 g/g. In one embodiment the hydrogel has a viscosity in the range of 4000-7000 Pa·s and a water retention value in the range of 40-50 g/g.

In one embodiment the medical hydrogel has a compression work in the range of 15-60 J/m$^2$. Such a compression work was found to provide a tough hydrogel which was not prone to chip or break when handled. The hydrogel could be detached from a wound or a skin as substantially intact. In one embodiment the hydrogel has a compression work in the range of 20-55 J/m$^2$. In one embodiment the hydrogel has a compression work in the range of 25-55 J/m$^2$. In one embodiment the hydrogel has a compression work in the range of 25-40 J/m². The compression work may be calculated from measurements made with a texture analyser as explained in the examples.

In one embodiment the nanofibrillar cellulose, when dispersed in water, provides a Brookfield viscosity of at least 500 mPa·s, at least 1000 mPa·s, or at least 1500 mPa·s, or at least 2000 mPa·s, such as at least 3000 mPa·s, up to 10000 mPa·s, or even up to 15000 mPa·s, measured at a consistency of 0.8% (w/w) and at 10 rpm. These values were found especially suitable for medical hydrogels in the tests. In one embodiment the nanofibrillar cellulose, when dispersed in water, provides a Brookfield viscosity in a range of 1000-10000 mPa·s, 1500-10000 mPa·s, or 2000-10000 mPa·s, or 3000-10000 mPa·s, or in a range of 1000-15000 mPa·s, 1500-15000 mPa·s, 2000-15000 mPa·s, or 3000-15000 mPa·s, measured at a consistency of 0.8% (w/w) and at 10 rpm In one embodiment the nanofibrillar cellulose in the medical hydrogel is anionically modified nanofibrillar cellulose. The anionically modified nanofibrillar cellulose can be fibrillated into a desired fibrillation degree and it forms a gel having desired properties as described herein.

The hydrogel to be used as a medical hydrogel needs to be homogenous. Therefore the method for preparing the medical hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the medical applications is obtained. The hydrogel may be further sterilized, for example by using heat and/or radiation, and/or by adding sterilizing agents, such as antimicrobials.

Medical Products

The medical products comprising the hydrogel may be used in several applications. One specific field is medical applications, wherein the materials are applied on living tissue, such as skin. The materials may be used in medical products, such as patches, dressings, bandages, filters and the like. The medical products may also be therapeutic products, such as therapeutic patches or gels containing medicament. In general the surface of the product comprising nanofibrillar cellulose will be in contact with the skin during the use. A surface of nanofibrillar cellulose may provide advantageous effects when it is in direct contact with the skin, for example it may promote healing of a wound or other damage on a skin, or it may promote delivery of substances from the medical product to the skin.

The term "wound" as used herein refers to any damages, injuries, diseases, disorders or the like on a tissue, such as skin, mucous membrane, or subcutaneous tissue including tendons, including open or closed wounds, wherein the healing of the wound is desired and may be promoted with the product described herein. The wound may be clean, contaminated, infected or colonized, wherein especially in the latter cases a therapeutic agent, such as an antibiotic, may be administered. Examples of open wounds include abrasions, avulsions, incisions, lacerations, puncture wounds and penetration wounds. Examples of closed wounds include hematomas, crush injuries, sewn wounds, grafts and any skin conditions, diseases or disorders. Examples of conditions, diseases or disorders of the skin include acne, infections, vesiculobullous diseases, cold sore, cutaneous candidiasis, cellulitis, dermatitis and eczema, herpes, hives, lupus, papulosquamous, urticaria and erythema, psoriasis, rosacea, radiation-related disorders, pigmentation, mucinoses keratosis, ulcer, atrophy, and necrobiosis, vasculitis, vitiligo, warts, neutrophilic and eosinophilic diseases, congenital, neoplasms and cancer, such as melanomas and tumours of epidermis or dermis, or other diseases or disorders of epidermis and dermis.

A medical product comprising a therapeutic agent may be provided, wherein the hydrogel comprising nanofibrillar cellulose contain(s) one or more therapeutic agent(s), such as a bioactive agent, a medicament or a drug. Also the term pharmaceutical agent may be used interchangeably instead of the term therapeutic agent. The therapeutic agent may be provided in the form of a salt, ester, amide, prodrug, conjugate, active metabolite, isomer, fragment, analog, or the like. Such agents are active or effective agents, which are usually present in effective amounts. Such an agent may be provided in a predetermined amount, for example in an amount configured to provide a desired dose of the agent during a certain time period, and/or configured to provide a desired effect on the target, such as skin or other tissue. The content of the therapeutic agent in the product may be for example in the range of 0.01-20% (w/w), such as 0.05-10% (w/w). In one embodiment the content of the therapeutic agent in the product is in the range of 0.1-5% (w/w), such as 0.1-3% (w/w), 0.5-3.5% (w/w) or 0.5-5% (w/w). Especially if the therapeutic agent is included, a controlled, sustained or prolonged release of the agent may be provided. The controlled release refers for example to obtaining a desired release rate and/or profile of an agent over a time period, which may be affected by the selection of the gel, for example the percentage of the gel or the thickness of the gel, the concentration or form of the releasable agent(s), presence of any auxiliary agents, or other conditions, such as pH, temperature and the like having an effect to the release rate and/or activity of the releasable agents. The therapeutic agents may be present in water-soluble form, fat-soluble form or in an emulsion, or in another suitable form. The therapeutic agent(s) may be for example mixed with the hydrogel before the gel is concentrated to the desired concentration, or before a homogenizing treatment, or the agent(s) may be impregnated into a ready gel product.

Examples of therapeutic or bioactive agents which may be administered by using the medical products described herein include proteins, peptides, carbohydrates, lipids, nucleic acids or fragments thereof, preferably as isolated; antibiotics, pain relievers, such as lidocaine; opioids, such as fentanyl or buprenorphine; nicotine; hormones, such as estrogen, contraceptives or androgens, such as testosterone; nitroglycerin; scopolamine; clonidine; antidepressants, such as selegiline; ADHD medication, such as methylphenidate; vitamins, such as B12 or cyanocobalamin; 5-hydroxytryptophan; Alzheimer's medication, such as rivastigmine; acne medication; antipsoriatics, glucocorticoids such as hydrocortisone; antiandrogens such as bifluranol, cyoctol, cyproterone, delmadinone acetate, flutimide, nilutamide and oxendolone; antiestrogens such as delmadinone acetate, ethamoxytriphetol, tamoxifen and toremifene; antimicrobial agents; anesthetics; analgesics; anti-inflammatory compounds or agents; antihistamines; beta-blockers; growth factors; immunomodulators or medication for treating diseases or disorders of a skin. Therapeutic agents may be used for example in medical patches, which may be used on healthy skin or on damaged skin, to provide a prolonged, sustained or extended release of the therapeutic agent from the patch, for example during a period of several hours, for up to 6, 12, 24 or even 48 hours.

"Prolonged release", also called as timed release, sustained release or extended release, refers to a drug, or to a carried impregnated with the drug, that is designed to deliver a dose of a medication over an extended period. The aim is to maintain drug concentration within the therapeutic window for maximum or desirable period of time. The terms are generally used in context of oral dosage forms. In addition to pills, capsules and injectable drug carriers (that often have an additional release function), forms of controlled release medicines include gels, implants and devices and transdermal patches. The definition in European Pharmacopoeia recites: "A prolonged-release dosage form is a modified-release dosage form showing a slower release of the active substance(s) than that of a conventional-release dosage form administered by the same route. Prolonged release is achieved by special formulation design and/or manufacturing method. Equivalent term: extended-release dosage form."

One embodiment provides the medical product comprising antibiotic agent. Such a product is especially suitable for treating wounds, wherein the wound treating properties are combined with antibiotic properties which prevents infections caused by harmful microbes in the wound. Examples of suitable antibiotics include especially topical antibiotics, such as bacitracin, erythromycin, clindamycin, gentamycin, neomycin, polymyxin, mupirocin, tetracycline, meclocycline, (sodium) sulfacetamide, benzoyl peroxide, and azelaic acid, and combinations thereof. Also other types of antibiotics, such as systemic antibiotics, may be provided, for example penicillins, such as phenoxymethylpenicillin, flucloxacillin and amoxicillin; cephalosporins, such as cefaclor, cefadroxil and cephalexin; tetracyclines, such as tetracycline, doxycycline and lymecycline; aminoglycosides, such as gentamicin and tobramycin; macrolides, such as erythromycin, azithromycin and clarithromycin; clindamycin; sulphonamides and trimethoprim; metronidazole and tinidazole; quinolones, such as ciprofloxacin, levofloxacin and norfloxacin.

Examples of androgens include boldenone, fluoxymesterone, mestanolone, mesterolone, methandrostenolone, 17-methyltestosterone, 17-alpha-methyltestosterone 3-cyclopentyl enol ether, norethandrolone, normethandrone, Oxandrolone, Oxymesterone, oxymetholone, Prasterone, Stanlolone, Stanozolol, testosterone, testosterone 17-chloral hemiacetal, testosterone 17-beta-cypionate, testosterone enanthate, testosterone nicotinate, testosterone pheynylacetate, testosterone propionate and tiomesterone.

Examples of antibiotics that may be included in the composition include aminoglycosides (e.g., tobramycin, amikacin, gentamicin, kanamycin, netilmicin, tobramycin, streptomycin, azithromycin, clarithromycin, erythromycin, neomycin, erythromycin estolate/ethylsuccinate, gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), cephalosporins (e.g., cephalexin, cephalothin, cefazolin, cefaclor, cefamandole, cefoxitin, cefuroxime, cefonicid, cefinetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), fluoroquinolones (e.g., ciprofloxacin), carbepenems (e.g., imipenem), tetracyclines (e.g., doxycycline, minocycline, tetracycline), macrolides (e.g., erythromycin and clarithromycin), monobactams (e.g., aztreonam), quinolones (e.g., fleroxacin, nalidixic acid, norfloxacin, ciprofloxacin, ofloxacin, enoxacin, lomefloxacin and cinoxacin), glycopeptides (e.g., vancomycin, teicoplanin), chloramphenicol, clindamycin, trimethoprim, sulfamethoxazole, nitrofurantoin, rifampin and mupirocin, and polymyxins, such as PMB, oxazolidinones, imidazoles (e.g., miconazole, ketoconazole, clotrimazole, econazole, omoconazole, bifonazole, butoconazole, fenticonazole, isoconazole, oxiconazole, sertaconazole, sulconazole and tioconazole), triazoles (e.g., fluconazole, itraconazole, isavuconazole, ravuconazole, posaconazole, voriconazole, terconazole and albaconazole), thiazoles (e.g., abafungin), and allylamines (e.g., terbinafine, naftifine and butenafine), echinocandins (e.g., anidulafungin, caspofunginand micafungin). Other antibiotics can include polygodial, benzoic acid, ciclopirox, tolnaftate, undecylenic acid, flucytosine or 5-fluorocytosine, griseofulvin, and haloprogin.

Antibiotics may be also used for treating acne, for example clindamycin, erythromycin, doxycycline, tetracycline etc. Also other agents may be used, such as benzoyl peroxide, salicylic acid, topical retinoid medicines, such as tretinoin, adapalene or tazarotene, azelaic acid, or androgen blockers such as spirolactone. Psoriasis may be treated for example with steroids, such as corticosteroids, moisturizers, calciprotriene, coal tar, vitamin D, retinoids, tazatorene, anthralin, salisylic acid, methotrexate, or cyclosporine. Insect bites or poison ivy exposure may be treated with agents such as hydrocortisone, emu oil, almond oil, ammonia, bisabolol, papain, diphenylhydramine, jewelweed extract or calamine. Some of these or other treatment agents may be also categorized as cosmetic agents.

Examples of antimicrobial agents that may be included in the composition include silver particles, particularly silver nanoparticles, agents or compounds that release silver ions, chlorhexidine gluconate, and polyhexamethylene biguanide.

Examples of anesthetics that may be included in the composition include procaine, benzocaine, chloroprocaine, cocaine, cyclomethycaine, dimethocaine, piperocaine, propoxycaine, procaine, novocaine, proparacaine, tetracaine, lidocaine, articaine, bupivacaine, cinchocaine, etidocaine, levobupivacaine, mepivacaine, prilocaine, ropivacaine, and trimecaine. In some embodiments, the anesthetic is a combination of lidocaine and prilocaine.

Examples of analgesics that may be included in the composition include opiates and analogues thereof. Exemplary opiates include morphine, codeine, oxycodone, hydrocodone, dihydromorphine, pethidine, buprenorphine, tramadol, fentanyl and venlafaxine.

Examples of anti-inflammatory compounds that may be included in the composition include hydrocortisone, cortisone, dexamethasone, fluocinolone, triamcinolone, medrysone, prednisolone, flurandrenolide, prednisone, halcinonide, methyl prednisolone, prednisone, halcinonide, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, acetosalicylic acid, salicylic acid, diflunisal, methyl salicylate, phenylbutazone, sulindac, mefenamic acid, meclofenamate sodium and tolmetin.

Examples of antihistamines that may be included in the composition include diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine and chlorpheniramine.

Examples of growth factors that may be included in the composition, include vascular endothelial growth factor ("VEGF"), nerve growth factor, such as NGF-beta, platelet derived growth factor (PDGF), fibroblast growth factors, including, for instance, aFGF and bFGF, epidermal growth factor (EGF), keratinocyte growth factor, tumor necrosis factor, transforming growth factors (TGF), including, among others, TGF-alpha and TGF-beta, including TGF-beta 1, TGF-beta 2, TGF-beta 3, TGF-beta 4, or TGF-beta 5, insulin-like growth factors-I and -II (IGF-I and IGF-II), des(1-3)-IGF-I (brain IGF-1), neurotrophin-3 (NT-3) and brain-derived neurotrophic factor (BDNF).

Examples of immunomodulators that may be included in the composition include cyclosporin A, guanylhydrazone, azathioprine, methotrexate, cycphosphamide and tacrolimus.

One embodiment provides a medical product, such as a dressing, a patch or a filter, comprising the hydrogel described herein.

One embodiment provides the hydrogel for use for treating and/or covering wounds. One embodiment provides the hydrogel for use for treating and/or covering skin wounds or other damages. One embodiment provides such a hydrogel for use as a dressing or a patch, or in a dressing or a patch, for treating and/or covering skin wounds or other damages.

One embodiment provides the hydrogel for use for treating open wounds such as abrasions, avulsions, incisions, lacerations, puncture wounds or penetration wounds. One embodiment provides such a hydrogel for use as a dressing or a patch, or in a dressing or a patch for treating open wounds such as abrasions, avulsions, incisions, lacerations, puncture wounds or penetration wounds. The open wounds may also be called deep wounds, or the open wounds may include deep wounds.

Deep wounds refer to wounds involving deeper cell membranes. By one definition, a deep wound is one that cuts deeper than ¼ of an inch (about 6.4 mm) beneath the surface of the skin. It may be possible that in deep wounds hair follicles and glands beneath the skin layers are damaged. In many cases, the patients' bodies grow scar tissues very fast, so that the deep wounds are not completely healed. Instead, only the surface of the wounds is healed, while the inner membranes are not completely formed yet. Deeper and in some cases dirtier and larger wounds are more susceptible to bacterial infection. As a result, this will delay the entire healing process. Deep wound healing process usually involves bleeding, inflammation, new tissue growth and scarring. By applying the hydrogel of the embodiments to the wound, it is possible to facilitate the healing process in one or more of these stages, preferably in all of them. The hydrogel helps to keep the wound moist, protects from infections, and provides a natural environment for healing.

One embodiment provides the hydrogel for use for treating and/or covering skin wounds covered with a graft, such as a skin graft. One embodiment provides the hydrogel for use as a dressing or a patch, or in a dressing or a patch, for treating and/or covering skin wounds covered with a graft, such as a skin graft.

One embodiment provides the hydrogel for use for administering therapeutic agent. In one example the hydrogel may be provided as such or for example in a patch. In one example the hydrogel may be provided in injectable form. One or more therapeutic agent(s) may be included, for example impregnated, in the hydrogel as described herein, and the administration to a patient may be dermal or transdermal.

One embodiment provides a cosmetic product, such as a dressing, a mask or a patch, comprising the hydrogel. Such a product may be called also as a cosmetic product. The product may be provided in various shapes, for example a mask may be designed to fit onto face, for example below eye or onto chin, nose or forehead. One embodiment provides the hydrogel for use as a cosmetic product. The product may be used for releasing one or more cosmetic agent(s) to the user, such as to the skin of the user. Such a cosmetic product may comprise one or more cosmetic agent(s). Cosmetic agent(s) may be included, for example impregnated, in the product wherefrom they will be released or delivered. The content of a cosmetic agent in the product may be for example in the range of 0.01-20% (w/w), such as 0.05-10% (w/w). In one embodiment the content of the cosmetic agent in the product is in the range of 0.1-5% (w/w), such as 0.1-3% (w/w), or 0.5-5% (w/w). The cosmetic agents may be present or provided in the product similarly as explained above for therapeutic agents, and vice versa. The cosmetic use may be analogous to medical use described herein, especially the administering of therapeutic agent. Cosmetic agents may be used also for cosmetically treating skin diseases or disorders, such as those mentioned herein. Such cosmetic products may be used for example for treating pimples, acneic skin, brown sports, wrinkles, oily skin, dry skin, aged skin, spider veins, after sun erythemas, black circles etc. Examples of cosmetic patches include skin cleansers, such as pore cleansers, blackhead removers, stretching stripes, short-term patch-like masks, short-term treatment patches and overnight treatment patches.

Examples of cosmetic agents include forms of vitamins and precursors thereof, such as vitamin A; for example retinoids, such as retinaldehyde (retinal), retinoic acid, retinyl palmitate and retinyl retinoate, ascorbic acid, alpha-hydroxy acids such as glycolic acid and lactic acid; glycols; biotechnology products; keratolytics; amino acids; antimicrobials; moisturizers; pigments; antioxidants; plant extracts; cleansing agents or make-up removers; anti-cellulite agents such as caffeine, carnitine, *Ginkgo biloba* and horse-chestnut; conditioners; fragrances such as aromatherapy agents and perfumes; humectants such as urea, hyaluronic acid, lactic acid and glycerine; emollients such as lanolin, triglycerides and fatty acid esters; FR scavengers, singlet oxygen scavengers, superoxide scavengers or hydrogen peroxide scavengers, such as ascorbic acid (vitamin C), glutathione, tocopherol (vitamin E), carotenoids, coenzyme Q10, bilirubin, lipoic acid, uric acid, enzyme mimetic agents, idebenone, polyphenols, selenium, spin traps such as phenyl butyl nitrone (PBN), protein methionine groups, superoxide dismutase, catalase, selenium peroxidases, heme oxygenases etc. or combinations thereof. The cosmetic agents may be present in water-soluble form, fat-soluble form or in an emulsion, or in another suitable form.

The medical or cosmetic hydrogels as described herein may be provided as incorporated or packed, such as packed in one or more sealed package(s), or in one or more application device(s), such as a syringe, an applicator, a pump or a tube containing the desired amount of the hydrogel, such as syringes of the size from 0.5 ml to 200 ml or even more. Preferably the package or the application device is sterile, sterilized or sterilizable. The application device(s) may be further packed in sealed package(s), such as plastic bags or the like, such as a plastic packing having a tearable part, for example paper or plastic sheet, such as packings generally used for syringes. The device may comprise a mouthpiece or nozzle for providing constant flow of the hydrogel in desired thickness and breadth and geometrics. These "ready for use" devices may be packed, sterilized and stored, and used when desired. These application devices may be incorporated in ready-to use kits.

One example provides a method for cosmetically treating skin, the method comprising applying the medical product described herein onto skin.

One embodiment provides the medical product described herein packed in a separate packing. Separate packings may be provided as a series of packings. Usually such packed products are provided as sterilized. The packing may be for example a plastic packing, such as a jar, a plastic bag, or a tube, such as a pressable tube, or a syringe.

One embodiment provides a kit comprising the medical product or the cosmetic product described herein, for example a packed product, wherein the kit may contain one or more of the packed products packed in one or more packings. The kit may also contain other materials or equipment, such as a container containing saline solution or the like for pretreating the product(s) prior to use, or an applicator, such as a spatula or the like.

One example provides a method for delivering substances to a subject, the method comprising providing the medical hydrogel, as described in the embodiments, containing one or more substance(s), such as therapeutic or cosmetic substance(s) or agent(s), and applying the hydrogel onto skin of the subject. The subject may be a patient or any other subject in need of the substance(s), such as human or animal. By applying the hydrogel onto the skin, the substance(s) will be delivered transdermally, preferably by controlled and/or prolonged release rate.

One example provides a method for treating skin wounds or other damages or injuries, the method comprising applying the medical product described herein onto the wound, damage, or injury. One specific example provides a method for treating skin wounds covered with a graft, such as a skin graft, for example a mesh graft or a full thickness graft, the method comprising applying the medical product described herein onto the graft.

Grafting refers to a surgical procedure to move tissue from one site to another on the body, or from another person, without bringing its own blood supply with it. Instead, a new blood supply grows in after it is placed. Autografts and isografts are usually not considered as foreign and, therefore, do not elicit rejection. Allografts and xenografts are recognized as foreign by the recipient and are rejected.

Skin grafting is often used to treat skin loss due to a wound, burn, infection, or surgery. In the case of damaged skin, it is removed, and new skin is grafted in its place. Skin grafting can reduce the course of treatment and hospitalization needed, and can also improve function and appearance. There are two types of skin grafts: Split-thickness skin grafts (epidermis+part of the dermis) and full-thickness skin grafts (epidermis+entire thickness of the dermis).

A mesh graft is a full- or partial-thickness sheet of skin that has been fenestrated to allow drainage and expansion. Mesh grafts are useful in many locations on the body because they conform to uneven surfaces. They can be placed in locations that have excessive motion because they can be sutured to the underlying wound bed. Additionally, their fenestrations provide outlets for fluid that may accumulate beneath the graft, which helps reduce tension and the risk of infection and improve vascularization of the graft.

Examples

Production of Nanofibrillar Cellulose

Birch cellulose pulp was anionically modified by "TEMPO" oxidation. Carboxylic acid content of the modified pulp was 1.06 mmol COOH/g pulp determined by conductometric titration The anionic pulp was dispersed to water to form dispersions at selected concentrations (solids content) in the range of 3.8-7.9%. The dispersions were run 3 times through a disperser (Atrex), through its series of counter rotating rotors, to fibrillate the pulp. The disperser used had a diameter of 850 mm and rotation speed used was 1800 rpm. Next the hydrogel was homogenized in a non-fibrillating homogenization treatment. As a result, cellulose hydrogel having the demanded properties was obtained.

The properties of the nanofibrillar hydrogels were studied with tests measuring water retention capacity, rheological properties and compression strength. Because these measurements do not necessarily fully reflect all the properties of the hydrogels, also user tests were conducted wherein persons skilled in the art evaluated the properties of the gels in more real-life situations by touching, moulding and applying different gels on skin.

Water Retention Capacity

Water retention capacity was measured according to the following procedure.

ÅAGWR (Åbo Akademi Gravitometric Water Retention) is a coating colour static water retention method developed by Åbo Akademi. ÅAGWR-Hydrogel is a hydrogel water retention capacity method developed for ÅAGWR device.

Liquid phase amount of the sample gone through membrane foil with certain time and pressure was measured. Absorbed water amount in hydrogel was calculated.

ÅAGWR device (FIG. 1) was used in the measurements. The device contains metal cylinders, a balancing plug, and a rubber measuring base. Whatman 17CHR blotting board and Whatman Nucleopore 0.4 μm membrane foils, diameter 47 mm were used, as well as a stopwatch and an analytical balance (accuracy 0.0001 g).

Dry content of the hydrogel was determined in oven by keeping the sample 4 hours in 105° C. temperature. Weigh of the hydrogel was determined before and after drying. The blotting board was cut in 57 mm×57 mm pieces.

The measurement procedure was as follows.

The hydrogel to be measured is completely mixed with a spoon. Pressure air is connected and adjusted to 0.5 bar as a measuring pressure of the ÅAGWR device. Two pieces of the balanced blotting board with wire side upwards are set on the rubber measuring base. A membrane foil glossy surface upwards is set on the blotting board. The metal cylinder is placed on the filter.

About 5 g hydrogel is dosed to the cylinder, and face-dressed against membrane by putting the balancing plug to the measuring cylinder for a couple of seconds. The rubber measuring base is set with filter and cylinder to the measuring table of the device and the measuring table is lifted (CYLINDER).

The rubber plug is set into place, pressure is connected on (PRESSURE) and stopwatch is started.

The pressure is let to interact 3 minutes, and then the pressure is disconnected (PRESSURE), the measuring table is lift down (CYLINDER) and the rubber measuring base is taken out of the measuring table. The cylinder with membrane foils is removed from the blotting board and the blotting boards are weighed with 0.1 g accuracy.

Two parallel measurements are carried out. If test results differ over 5% from each other, more parallel measurements (max 3 measurements/sample) shall be carried out.

Calculation and Reporting of Results $$X(g/g) = \frac{(A - B) - (a - b)}{(A \times C)/100}$$

X Hydrogel water retention capacity, g/g
A Hydrogel wet weigh, g
B Hydrogel dry weigh, g a Blotting board wet weigh, g
b Blotting board dry weigh, g
C Hydrogel dry content Hydrogel water retention capacity test results is average of two parallel measurements. Measurement accuracy is 0.1 g/g.

If test results differ over 5% from each other, more parallel measurements (max 3 measurements/sample) shall be carried out.

Rheological Measurements

The rheological measurements were performed at 37° C. with HAAKE Viscotester iQ Rheometer (Thermo Fisher Scientific, Karlsruhe, Germany) equipped with a Peltier system for temperature control. Results were analyzed with HAAKE RheoWin 4.0 software (Thermo Fisher Scientific). Parallel 35 mm diameter steel plate-and-plate geometry was used with a 1 mm gap in all measurements. Before each measurement, the samples were allowed to rest for 5 min at 37° C. Controlled stress amplitude sweeps were performed to determine the linear viscoelastic region for different NFC hydrogel formulations. Constant angular frequency $\omega=1$ Hz and oscillatory stress between 0.0001-500 Pa was used in all amplitude sweeps. The chosen oscillatory stresses for frequency sweeps were $\tau=50$ Pa (3% NFC hydrogel), $\tau=80$ Pa (5.7% NFC hydrogel) and $\tau=100$ Pa (6.5% NFC hydrogel) and the angular frequency range was 0.6-125.7 rads$^{-1}$. Shear viscosity was measured by increasing the shear rate from 0.1 to 1000 1/s.

The settings used in the rheology measurements were as follows:

Amplitude: CS mode→linear viscoelastic region
  shear stress amplitude sweep, 37° C., t=300 s hold→osc amp sweep, $\tau=0.0001$-500 Pa, f=1 Hz (6.2832 rad/s)
  log, 16 steps Frequency: CS mode
  frequency sweep with constant shear stress, 37° C., t=300 s hold,
  $\tau=50$ Pa (3.2%), $\tau=80$ Pa (5.7%) and $\tau=100$ Pa (6.8%)
  f=0.1-20 Hz (i.e. $\omega=0.6283$ rad/s-125.7 rad/s)
  log, 16 steps Viscosity: CR mode
shear rate (1/s)=0.1-1000

TABLE 1

| Sample | Solids content, % | Turbidity (HACH), NTU | Brookfield 10 rpm, 0.8%, mPa·s | Viscosity at own conc. shear rate 0.1 | Compression work J/m$^2$ "Toughness" | Water retention value g/g |
|---|---|---|---|---|---|---|
| 1 | 3.8 | 21 | 5680 | 2190 | 15.5 | 47.0 |
| 2 | 5.4 | 22 | 1580 | 3765 | 28.1 | 44.3 |
| 3 | 6.5 | 23 | 1090 | 6313 | 35.9 | 44.8 |
| 4 | 6.6 | 22 | 1080 | 6633 | 37.4 | 47.2 |
| 5 | 7.9 | 25 | 380 | 9196 | 53.2 | 44.1 |
| Purilon | | | | | | 20.6 |

TABLE 2

Measurements for the Sample 1 (11885)

| Viscosity average | Viscosity StDev | Stress average | Stress StDev | Shear rate | Shear rate variation |
|---|---|---|---|---|---|
| 2190.33 | 141.85 | 219.15 | 14.26 | 0.1 | 3.8E−05 |
| 1052.62 | 30.93 | 194.72 | 5.74 | 0.2 | 3.4E−05 |
| 539.39 | 18.34 | 184.23 | 6.26 | 0.3 | 7.6E−06 |
| 295.85 | 16.92 | 186.70 | 10.66 | 0.6 | 7.8E−05 |
| 170.83 | 19.49 | 199.19 | 22.71 | 1.2 | 6.8E−05 |
| 91.46 | 25.80 | 197.06 | 55.58 | 2.2 | 7.4E−05 |
| 48.75 | 7.61 | 194.10 | 30.30 | 4.0 | 1.3E−04 |
| 31.33 | 3.59 | 230.50 | 26.38 | 7.4 | 5.3E−05 |
| 20.43 | 2.28 | 277.78 | 31.05 | 13.6 | 7.0E−05 |
| 11.77 | 1.95 | 295.69 | 49.05 | 25.1 | 1.9E−04 |
| 6.08 | 1.62 | 282.01 | 75.15 | 46.4 | 1.8E−04 |
| 3.11 | 0.73 | 267.13 | 62.43 | 85.8 | 2.4E−04 |
| 1.37 | 0.30 | 217.30 | 48.12 | 158.5 | 3.0E−04 |
| 0.40 | 0.14 | 116.98 | 40.77 | 292.9 | 3.7E−04 |
| 0.04 | 0.02 | 22.57 | 10.68 | 541.2 | 9.3E−05 |
| 0.01 | 0.01 | 14.96 | 7.73 | 1000.0 | 1.3E−04 |

TABLE 3

Measurements for the Sample 2 (11886)

| Viscosity average | Viscosity StDev | Stress average | Stress StDev | Shear rate | Shear rate variation |
|---|---|---|---|---|---|
| 3764.897 | 291.0421 | 376.9458 | 29.04821 | 0.100122 | 7.54078E−05 |
| 1687.184 | 161.4996 | 312.4261 | 29.9852 | 0.185173 | 0.000131793 |
| 798.5763 | 97.04332 | 272.8259 | 33.15118 | 0.34164 | 5.16172E−05 |
| 420.5153 | 83.6605 | 265.3846 | 52.79296 | 0.631095 | 1.06927E−05 |
| 236.0018 | 49.1284 | 275.1997 | 57.3145 | 1.166077 | 0.000117202 |
| 132.0042 | 6.231784 | 284.4135 | 13.43811 | 2.154577 | 0.000138633 |
| 82.41929 | 4.119943 | 328.1303 | 16.40659 | 3.98123 | 0.000104417 |
| 53.30588 | 2.706472 | 392.1537 | 19.91318 | 7.356667 | 0.000134247 |
| 33.26296 | 1.014422 | 452.174 | 13.78369 | 13.59392 | 0.000238689 |
| 20.29607 | 1.052873 | 509.83 | 26.45215 | 25.11964 | 0.000221541 |
| 11.01815 | 0.823503 | 511.428 | 38.22503 | 46.41685 | 8.10946E−05 |
| 4.350177 | 0.353293 | 373.1205 | 30.30129 | 85.77135 | 0.000581225 |
| 1.817503 | 0.541681 | 288.0573 | 85.85146 | 158.4907 | 8.66025E−06 |
| 0.666109 | 0.442982 | 195.082 | 129.735 | 292.8682 | 0.000479631 |
| 0.03497 | 0.012203 | 18.92478 | 6.60396 | 541.1712 | 9.3179E−05 |
| 0.006952 | 0.003993 | 6.95197 | 3.993338 | 1000.003 | 6.15007E−05 |

TABLE 4

Measurements for the Sample 3 (11887)

| Viscosity average | Viscosity StDev | Stress average | Stress StDev | Shear rate | Shear rate variation |
|---|---|---|---|---|---|
| 6313.265 | 520.4828 | 633.1879 | 51.27737 | 0.100304 | 0.000260571 |
| 2822.157 | 255.5567 | 522.8187 | 47.46594 | 0.185252 | 8.03762E−05 |
| 1380.253 | 132.9933 | 471.7065 | 45.59369 | 0.341747 | 0.00010018 |
| 741.2196 | 87.09105 | 467.7734 | 54.98204 | 0.631084 | 2.69072E−05 |
| 425.4392 | 63.12846 | 496.0963 | 73.62272 | 1.166078 | 4.44672E−05 |
| 241.8347 | 10.4951 | 521.0842 | 22.66832 | 2.154706 | 0.000222552 |
| 149.1667 | 7.960825 | 593.8617 | 31.6809 | 3.981198 | 9.03899E−05 |
| 90.03645 | 6.115975 | 662.4033 | 45.02161 | 7.357043 | 0.000300711 |
| 51.84418 | 0.150818 | 704.7762 | 2.04557 | 13.59412 | 0.000189985 |
| 29.85361 | 0.60282 | 749.9189 | 15.15063 | 25.11987 | 0.000624882 |
| 12.80201 | 1.833309 | 594.2372 | 85.08475 | 46.4176 | 0.00100114 |
| 4.925564 | 1.896935 | 422.47 | 162.7006 | 85.77099 | 0.000667094 |
| 1.5616 | 0.808498 | 247.5 | 128.1401 | 158.4912 | 0.000426924 |
| 0.423919 | 0.250556 | 124.1525 | 73.37993 | 292.8678 | 0.000702228 |
| 0.025599 | 0.013757 | 13.85331 | 7.444675 | 541.1713 | 0.000196088 |
| 0.006126 | 0.002029 | 6.125714 | 2.029092 | 1000.003 | 9.3179E−05 |

TABLE 5

Measurements for the Sample 4 (11888)

| Viscosity average | Viscosity StDev | Stress average | Stress StDev | Shear rate | Shear rate variation |
|---|---|---|---|---|---|
| 6633.142 | 574.0153 | 664.8715 | 58.32832 | 0.100228 | 0.000114669 |
| 3234.298 | 279.1092 | 598.8826 | 51.57067 | 0.185168 | 5.95343E−05 |
| 1549.221 | 155.9001 | 529.6142 | 53.35466 | 0.341856 | 4.57092E−05 |
| 755.6112 | 51.18714 | 476.9888 | 32.36837 | 0.631259 | 7.95047E−05 |
| 398.9973 | 21.58989 | 465.3127 | 25.21272 | 1.166202 | 0.000228985 |
| 221.7749 | 16.73353 | 477.8331 | 36.03532 | 2.15459 | 9.90774E−05 |
| 135.6502 | 13.88256 | 540.0552 | 55.27127 | 3.981232 | 2.02567E−05 |
| 82.85664 | 8.139523 | 609.5607 | 59.89282 | 7.356802 | 0.000151337 |
| 49.84483 | 4.982574 | 677.5893 | 67.72705 | 13.59398 | 0.000257984 |
| 28.54281 | 2.844012 | 716.9934 | 71.43718 | 25.11994 | 0.00036951 |
| 13.17069 | 2.446373 | 611.3522 | 113.5483 | 46.41771 | 0.000559718 |
| 4.724588 | 0.815982 | 405.2322 | 69.98691 | 85.77091 | 0.000420952 |
| 1.42796 | 0.153366 | 226.3192 | 24.30676 | 158.4914 | 0.000255129 |
| 0.274805 | 0.085586 | 80.48146 | 25.06529 | 292.8674 | 0.000199773 |
| 0.016756 | 0.003938 | 9.068068 | 2.131106 | 541.1712 | 7.04367E−05 |
| 0.003367 | 0.00427 | 3.366703 | 4.269923 | 1000.003 | 0.000126982 |

TABLE 6

Measurements for the Sample 5 (11889)

| Viscosity average | Viscosity StDev | Stress average | Stress StDev | Shear rate | Shear rate variation |
|---|---|---|---|---|---|
| 9196.109 | 555.0525 | 921.0544 | 55.25668 | 0.100158 | 8.09588E−05 |
| 4473.872 | 348.1352 | 829.0122 | 64.68662 | 0.185299 | 4.46356E−05 |
| 2198.636 | 155.0183 | 751.5817 | 53.04701 | 0.341839 | 3.02379E−05 |
| 1127.663 | 65.69769 | 711.9123 | 41.58304 | 0.631313 | 0.000167359 |
| 598.5063 | 24.98993 | 698.0021 | 29.1481 | 1.16624 | 6E−05 |
| 343.6813 | 20.05878 | 740.5316 | 43.20442 | 2.154706 | 6.54243E−05 |
| 209.3614 | 21.22802 | 833.5355 | 84.49283 | 3.981331 | 0.000123618 |
| 128.7972 | 19.96781 | 947.5583 | 146.8817 | 7.356991 | 0.000467023 |
| 73.18917 | 7.222437 | 995.0002 | 98.22383 | 13.59488 | 0.000611708 |
| 42.37427 | 6.667042 | 1064.486 | 167.4746 | 25.12106 | 0.000946355 |
| 17.71857 | 2.804546 | 822.4858 | 130.1773 | 46.41947 | 0.001476698 |
| 5.030325 | 1.402609 | 431.4648 | 120.3101 | 85.77256 | 0.001032494 |
| 0.664098 | 0.064553 | 105.2542 | 10.23126 | 158.492 | 0.000650989 |
| 0.155852 | 0.085644 | 45.64374 | 25.08244 | 292.8669 | 0.000521891 |
| 0.021787 | 0.013683 | 11.79071 | 7.404794 | 541.1712 | 0.000126982 |
| 0.005785 | 0.002712 | 5.784904 | 2.712572 | 1000.003 | 0.000357797 |

Figure 3:
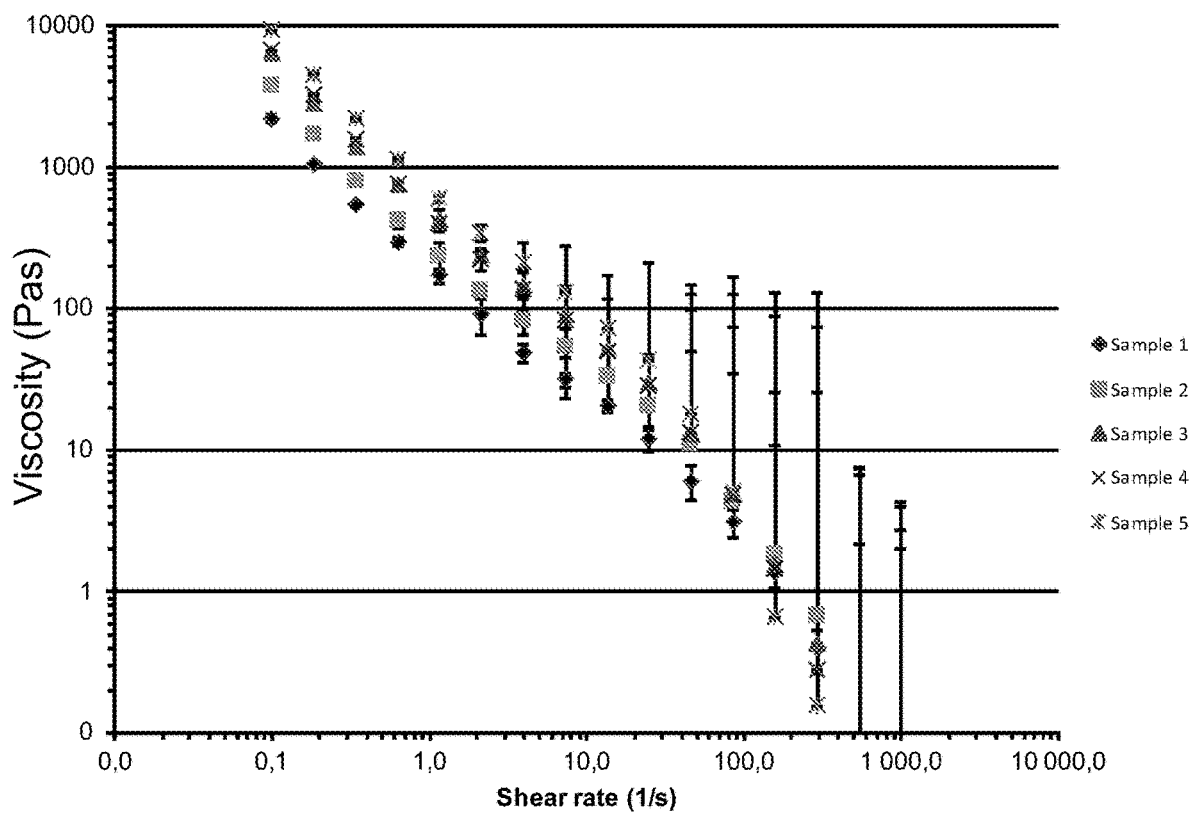
FIG. 3 shows a graph of measurement results from shear rate tests

The measurement results are presented a graphs in FIG. 3.

Compression Work

The objective of this work was to find out whether a compression test performed with a Texture Analyser could be a suitable method for characterising the texture of homogenized nanocellulose cylinders. The dry matter (solids) content of the tested samples varied between 3.2% and 7.9%.

The results revealed great differences in toughness and strength between the samples. The repeatability of the measurements was at a good level, especially for the samples of higher dry matter content. The toughness of the homogenized samples increased almost linearly with increasing dry matter content.

Methods

Figure 2:
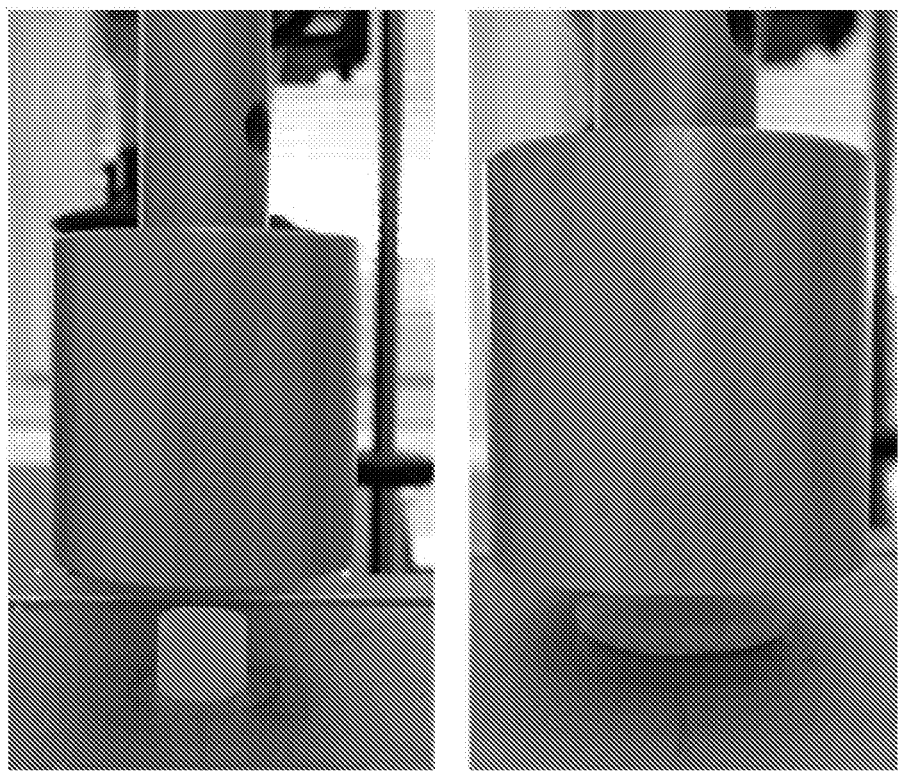
FIG. 2 shows a cylindrical probe of an Texture Analyser used in the tests

For the texture analysis, homogenized cylindrical nanocellulose bars with a diameter of 13 mm were obtained. From these bars about 10 mm long pieces were carefully cut with a sharp knife. Samples were allowed to equilibrate at room temperature (~22° C.) for at least one hour before the measurements. These cylindrical samples (diameter 13 mm, height 1 mm) were compressed with a Texture Analyser device (TA.XTPlus, Stable Micro Systems Ltd, UK) equipped with a cylindrical probe as shown in FIG. 2. The diameter of the aluminium probe was 45 mm. A 5 kg load cell was used in the measurements. The samples were compressed at a rate of 1 mm/s to a strain of 80%, i.e. the compression distance was 80% of the initial height of the samples. The force required for the compression was recorded as function of time/compression distance. The measurement was started when a trigger force of 5 g was exceeded. Five replicates were measured for each sample batch.

The raw data, i.e. compression force as function of distance and strain was analysed. Some variability was seen in the force-distance curves, which originates from small differences in sample height. Cutting samples of equal height was especially challenging for the soft samples with the lowest dry matter content (samples 6 and 11). When the compression distance was plotted as % strain (relative to initial sample height), the variability was considerably reduced. The force-strain (or force-distance) curves were of similar shape for all samples. At first, the force increased almost linearly with strain. Then at higher strains a decrease in the slope of the curve was observed, which was most probably caused by some sort of breakdown of the gel structure. For some samples the force was kept at an almost constant level at intermediate strains. Finally, at the highest strains a dramatic increase in force occurred when the probe started to get very close to the base plate.

Figure 4:
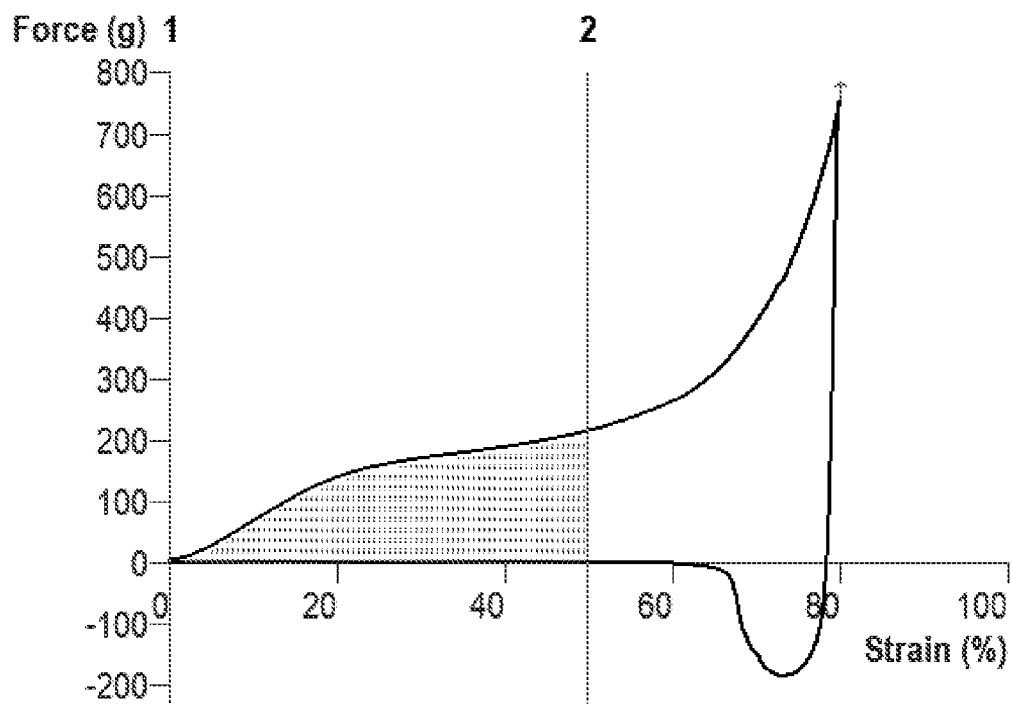
FIG. 4 shows calculation of the area under force-strain curve, i.e. compression work.
Figure 5:
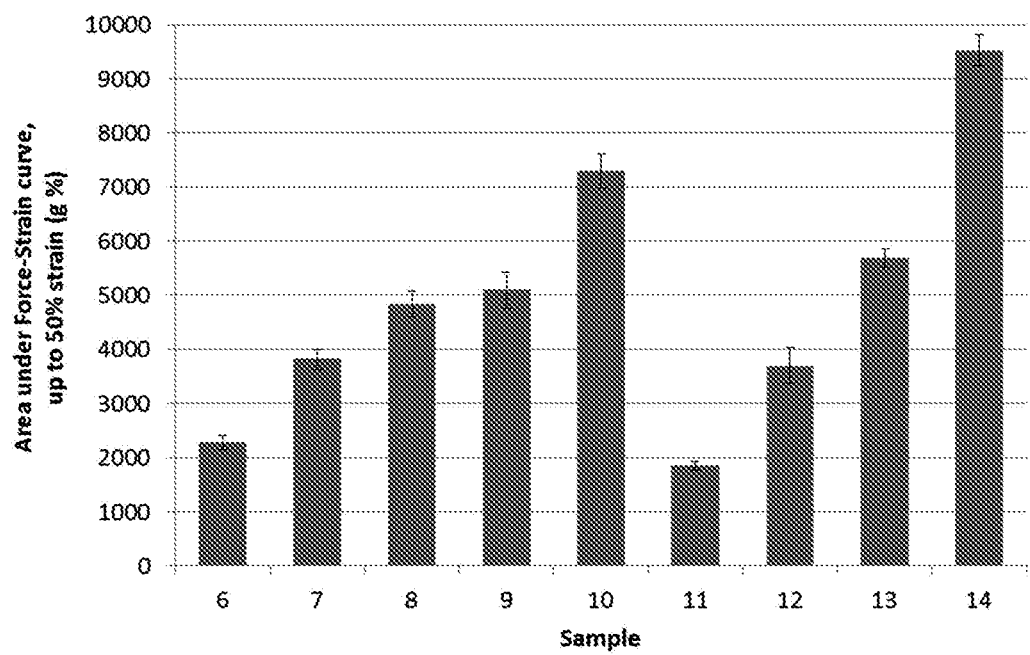
FIG. 5 shows the "toughness", i.e. the area under force-strain curve until 50% compression, of homogenized nanocellulose samples.
Figure 6:
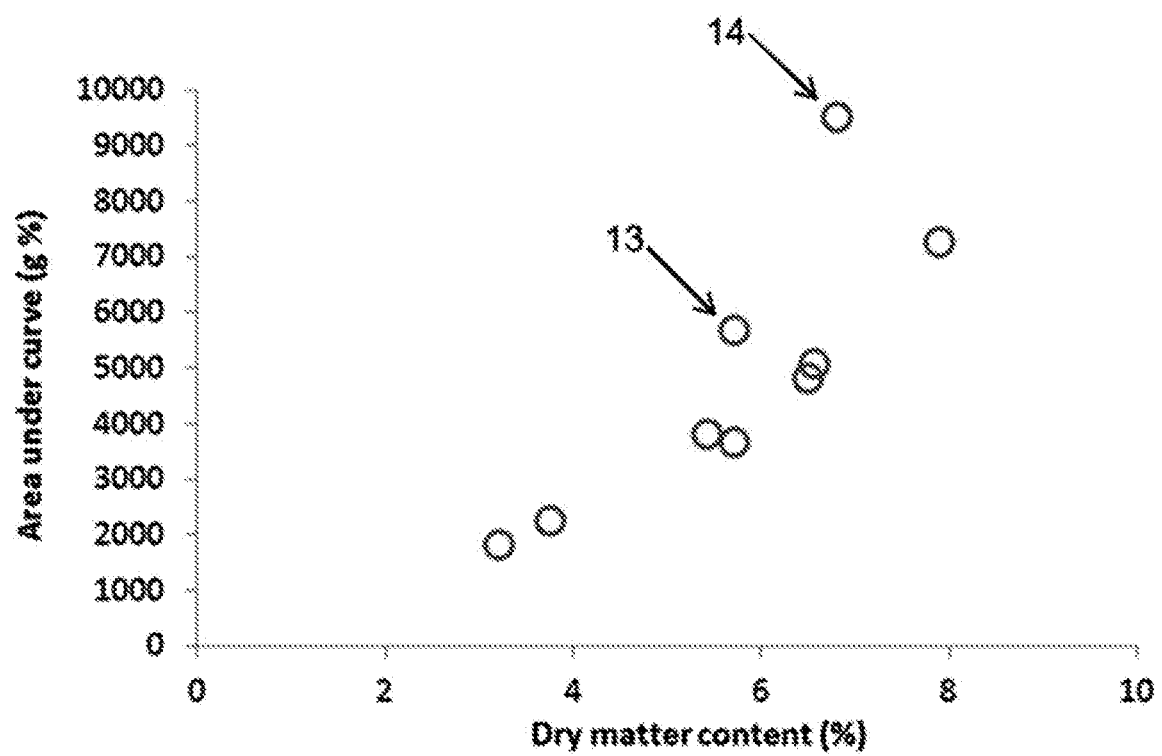
FIG. 6 shows the dependence of the area under the curve values ("toughness") on dry matter content of homogenized nanocellulose samples.

From the measurement curves of each sample, which showed clear differences between the softest and strongest samples, the area under the curve until 50% strain, i.e. compression work, was calculated as shown in FIG. 4, which can be taken as a measure of sample toughness. The calculated values are for all samples shown in FIG. 5 as "Area under Force-Strain curve, up to 50% strain (g %)". The "toughness" of samples 6-10 increased almost linearly with increasing dry matter content of the samples (FIG. 6). Sample 14 was a clear outlier, which may be explained by a difference in the raw material used as compared to the other samples. The nanocellulose used for sample 14 was not fresh, but had already previously been processed with the device used for homogenization. The samples with equal dry matter content (8 and 9) also showed similar "toughness" values.

In addition to the area under the curve, also the force at 10%, 50% and 80% strain were calculated from the force-strain curves (Table 7). The force values showed very good correlation with the determined area under the curve until 50% strain and did therefore not provide much extra information about differences in strength between the samples.

TABLE 7

Correlations of force at 10% (F10), 50% (F50) and 80% (F80) strain with area under curve until 50% compression (A50).

| | F10 | F50 | F80 | A50 |
| --- | --- | --- | --- | --- |
| F10 | 1 | | | |
| F50 | 0.979 | 1 | | |
| F80 | 0.982 | 0.999 | 1 | |
| A50 | 0.986 | 0.998 | 0.999 | 1 |

The compression test performed with a Texture Analyser appears to be an suitable method for characterising the texture of homogenized nanocellulose cylinders. The repeatability of the measurements was at a good level, especially for the samples of higher dry matter content. The toughness and strength of the homogenized samples were found to increase almost linearly with increasing dry matter content.

User Tests

Applicability of the nanocellulose hydrogel prototypes for wounds was evaluated by evaluation panels consisted of professional wound healing nurses in Finnish hospitals. The number of the nurses was 10. The nurses evaluated the following key properties of hydrogels.

Solidity i.e. the hydrogel should not flow by itself.

Non-stickiness i.e. the hydrogel should not stick to user's skin or gloves when applying and is easy to remove from a wound.

Formability i.e. the hydrogel should be shapeable for example into a deep wound.

Detachability i.e. the hydrogel should be removable as intact as possible from the wound.

The hydrogel prototypes were packed to 20 ml syringes from which the nurses dispensed the prototypes. Two different commercial hydrogels were used as references. Commercial 1 (Purilon) gel consists of purified water, sodium carboxymethylcellulose, and calcium alginate. Commercial 2 (Hydrosorb) gel is a hydrogel containing Ringers solution, glycerol, hydroxyethyl cellulose, and carboxymethyl cellulose.

After handling and evaluation they rated the prototypes to the evaluation table. The rating in the evaluation was scaled from 1 to 5: 1=Very poor; 2=Poor; 3=Satisfied; 4=Good; 5=Very good. The result table 8 shows average ratings for each hydrogels.

TABLE 8

User evaluation of different hydrogels.

| | Sample 1 | Sample 2 | Sample 4 | Sample 5 | Commercial 1 | Commercial 2 |
| --- | --- | --- | --- | --- | --- | --- |
| Solidity | 2.2 | 3.3 | 3.9 | 2.1 | 3.4 | 2.7 |
| Non-stickiness | 2.9 | 3.2 | 4.0 | 4.0 | 2.2 | 2.4 |
| Formability | 2.8 | 3.7 | 4.1 | 2.8 | 3.3 | 3.5 |
| Detachability | 3.5 | 3.7 | 4.3 | 4.2 | 2.7 | 2.8 |
| Average | 2.9 | 3.5 | 4.1 | 3.3 | 2.9 | 2.9 |

The invention claimed is:

1. A medical hydrogel comprising nanofibrillar cellulose, wherein the hydrogel has a solids content in the range of 4-8% (w/w) and a viscosity in the range of 2500-9000 Pa·s measured at a solids content of 4-8% (w/w), at 37° C. and a shear rate of 0.1 s$^{-1}$, and a water retention value in the range of 30-100 g/g, wherein the nanofibrillar cellulose is anionically modified via 2,2,6,6-tetramethylpiperidinyl-1-oxy (TEMPO) oxidation.

2. The medical hydrogel of claim 1, wherein the hydrogel has a solids content in the range of 4.5-8% (w/w).

3. The medical hydrogel of claim 1, wherein the hydrogel has a compression work in the range of 15-60 J/m$^2$.

4. The medical hydrogel of claim 1 containing one or more therapeutic agent(s).

5. A method for preparing a medical hydrogel, the method comprising
providing wood pulp,
anionically modifying the pulp, via 2,2,6,6-tetramethylpiperidinyl-1-oxy (TEMPO) oxidation,
disintegrating the pulp until nanofibrillar cellulose is obtained,
forming the nanofibrillar cellulose into a hydrogel, wherein the hydrogel has a solids content in the range of 4-8% (w/w) and a viscosity in the range of 2500-9000 Pas measured at a solids content of 4-8% (w/w), at 37° C. and a shear rate of 0.1 s$^{-1}$, and a water retention value in the range of 30-100 g/g.

6. The method of claim 5, wherein the hydrogel has a solids content in the range of 4.5-8% (w/w).

7. The method of claim 5, wherein the hydrogel has a compression work in the range of 15-60 J/m$^2$.

8. The method of claim 5, wherein the obtained nanofibrillar cellulose, when dispersed in water, provides a Brookfield viscosity of 500-10000 mPa·s, measured at a consistency of 0.8% (w/w) and at 10 rpm.

9. A kit containing the medical hydrogel of claim 1 packed in one or more sealed package(s), or in one or more application device(s) selected from a syringe, an applicator, a pump, and a tube.

10. A method for treating skin wounds or other damages or injuries, the method comprising applying the medical hydrogel of claim 1 onto the wound, damage, or injury.

11. The method of claim 10, wherein the skin wound is an open wound selected from abrasions, avulsions, incisions, lacerations, puncture wounds or penetration wounds.

12. The method of claim 10, wherein the skin wound is covered with a skin graft, and the method comprises applying the medical hydrogel onto the skin graft.

13. The medical hydrogel of claim 1, wherein the hydrogel has a solids content in the range of 5-7% (w/w), a viscosity in the range of 3000-8000 Pa-s, measured at a solids content of 5-7% (w/w), at 37° C. and a shear rate of 0.1 s$^{-1}$, and a water retention value in the range of 40-50 g/g.

14. The medical hydrogel of claim 1, wherein the hydrogel has a compression work in the range of 25-40 J/m$^2$.

15. The method of claim 5, wherein the hydrogel has a solids content in the range of 5-7% (w/w), a viscosity in the range of 3000-8000 Pa-s, measured at a solids content of 5-7% (w/w), at 37° C. and a shear rate of 0.1 s$^{-1}$, and a water retention value in the range of 40-50 g/g.

16. The method of claim 5, wherein the hydrogel has a compression work in the range of 25-40 J/m$^2$.

* * * * *